US007072721B1

(12) United States Patent
Trent

(10) Patent No.: US 7,072,721 B1
(45) Date of Patent: Jul. 4, 2006

(54) ELECTRODE VEST FOR ELECTRICAL STIMULATION OF THE ABDOMEN AND BACK

(75) Inventor: Cecilio Trent, 153 Lott, Apartment No. 1, Brooklyn, NY (US) 11226

(73) Assignee: Cecilio Trent, Brooklyn, NY (US)

( * ) Notice: Subject to any disclaimer, the term of this patent is extended or adjusted under 35 U.S.C. 154(b) by 605 days.

(21) Appl. No.: 10/285,420

(22) Filed: Nov. 1, 2002

(51) Int. Cl.
A61N 1/00 (2006.01)
A61N 1/04 (2006.01)
A61N 1/05 (2006.01)
A61N 1/06 (2006.01)

(52) U.S. Cl. ..................... 607/149; 600/382
(58) Field of Classification Search ............... 607/149; 600/382, 384, 386, 388, 389, 393
See application file for complete search history.

(56) References Cited

U.S. PATENT DOCUMENTS

| 3,559,640 | A | * | 2/1971 | Beckett ..................... 602/4 |
| 3,610,250 | A | * | 10/1971 | Sarbacher ................. 607/149 |
| 4,583,547 | A | | 4/1986 | Granek et al. |
| 4,708,149 | A | | 11/1987 | Axelgaard et al. |
| 4,785,813 | A | | 11/1988 | Petrofsky |
| 4,796,631 | A | | 1/1989 | Grigoryev |
| 5,018,521 | A | * | 5/1991 | Campbell .................. 607/98 |
| 5,078,134 | A | * | 1/1992 | Heilman et al. ............ 607/4 |
| 5,092,329 | A | * | 3/1992 | Graupe et al. ............. 607/66 |
| 5,133,354 | A | | 7/1992 | Kallok |
| 5,363,858 | A | * | 11/1994 | Farwell ..................... 600/544 |
| 5,443,494 | A | | 8/1995 | Paolizzi et al. |
| 5,487,759 | A | | 1/1996 | Bastyr et al. |
| 5,575,809 | A | | 11/1996 | Sasaki |
| 5,814,093 | A | | 9/1998 | Stein |
| 5,857,984 | A | | 1/1999 | deBoer et al. |
| D420,138 | S | | 2/2000 | Robinette |
| 6,065,154 | A | * | 5/2000 | Hulings et al. ............. 2/102 |
| 6,151,528 | A | | 11/2000 | Malda |
| 6,161,044 | A | * | 12/2000 | Silverstone ................ 607/45 |
| 6,236,890 | B1 | | 5/2001 | Oldham |
| 6,254,556 | B1 | | 7/2001 | Hansen et al. |

* cited by examiner

Primary Examiner—Mark Bockelman
Assistant Examiner—Frances P. Oropeza
(74) Attorney, Agent, or Firm—Carlos R. Villamar; Nixon Peabody, LLP

(57) ABSTRACT

A vest for providing electrical stimulation is disclosed. The vest includes front and rear sections and a controller. Left front and right front electrodes are provided on interior surfaces of the front section, and left rear and right rear electrodes are provided on interior surfaces of the rear section. The controller is provided on an exterior surface of the front section and provides selectively adjustable electrical pulse signals to the electrodes via wires routed over the exterior surface of the front and rear sections to the electrodes through respective openings provided in the front and rear sections. The electrodes and the front and rear sections include means for positional adjustment of the electrodes on the interior surfaces of the front and rear sections. The vest can be used for electrical stimulation of muscles or nerves of the abdomen and back for users having varying body types and sizes.

7 Claims, 4 Drawing Sheets

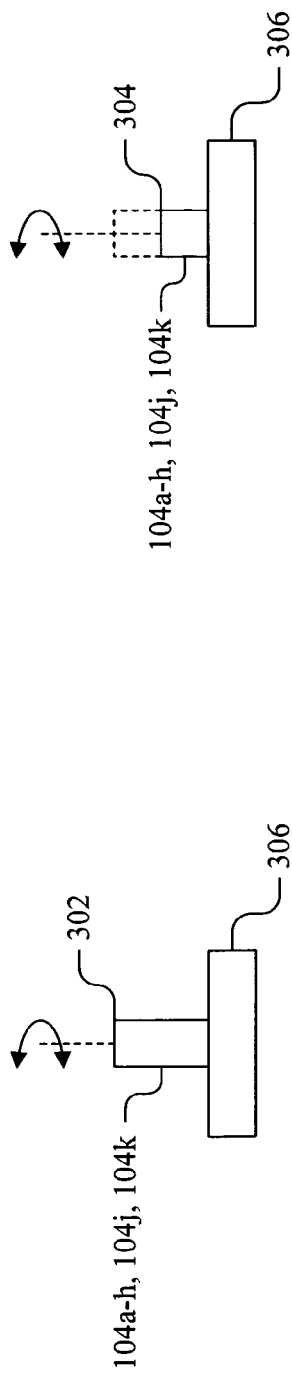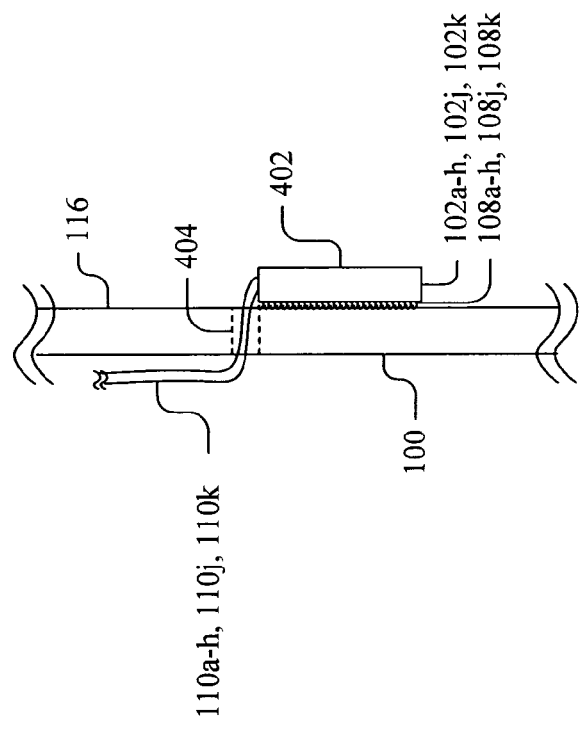

ELECTRODE VEST FOR ELECTRICAL STIMULATION OF THE ABDOMEN AND BACK

FIELD OF THE INVENTION

The present invention generally relates to electrical stimulation devices, and, more particularly, to an electrode vest for electrical stimulation of the abdomen and back.

DISCUSSION OF THE BACKGROUND

Over the years, various types of devices for electrical stimulation of muscles and/or nerves have been developed. These devices can be used for increasing muscle tone, physical therapy, repairing damaged nerves, etc., of users. However, some of the previous attempts, although fulfilling their various objects, suffer from problems resulting in their lack of acceptance into the consumer market place.

For example, U.S. Pat. No. 4,708,149 to Axelgaard et al., U.S. Pat. No. 4,785,813 to Petrofsky, U.S. Pat. No. 4,796,631 to Grigoryev, U.S. Pat. No. 5,133,354 to Kallok, and U.S. Pat. No. 6,236,890 to Oldham are directed to muscle and/or nerve electrical stimulation devices that include electrodes that are adhered onto or stabbed into the skin over the muscle or nerve being stimulated. However, such devices suffer from a range of problems, including, for example, the electrodes becoming de-attached from the skin during movement, the devices being relatively difficult to manufacture, etc.

U.S. Pat. No. 3,610,250 to Sarbacher, U.S. Pat. No. 4,583,547 to Grannek et al., U.S. Pat. No. 5,133,354 to Kallok, U.S. Pat. No. 5,487,759 to Bastyr et al., U.S. Pat. No. 5,575,809 to Sasaki, U.S. Pat. No. 5,814,093 to Stein, U.S. Pat. No. 5,857,984 to deBoer et al., and U.S. Pat. No. 6,151,528 to Maida are directed to muscle and/or nerve electrical stimulation devices that include electrodes that are incorporated within a garment, brace, belt, etc. However, such devices suffer from various problems, including, for example, the devices with integral electrodes being relatively difficult to manufacture and having to be custom-made for varying body types and sizes, the devices with fixed electrode positions providing inadequate muscle stimulation for varying body types and sizes, the devices lacking electrode placement for optimal abdomen and back muscle or nerve stimulation for varying body types and sizes, etc.

SUMMARY OF THE INVENTION

Therefore, there is a need for an electrical stimulation device that does not suffer from the problems with the background art devices, that firmly secures electrodes to the muscles or nerves during user movement, that is relatively easy to manufacture for varying body types and sizes, that includes variable electrode positions for accommodating varying body types and sizes, and that provides adjustable placement of electrodes for optimal abdomen and back muscle or nerve stimulation for varying body types and sizes.

The above and other needs are addressed by providing a vest having adjustable electrodes for electrical muscle or nerve stimulation. The vest includes front and rear sections and a controller. Left front and right front electrodes are provided on interior surfaces of the front section, and left rear and right rear electrodes are provided on interior surfaces of the rear section. The controller is provided on an exterior surface of the front section and provides selectively adjustable electrical pulse signals to the electrodes via wires routed over the exterior surface of the front and rear sections to the electrodes through respective openings provided in the front and rear sections. The electrodes and the front and rear sections include means for positional adjustment of the electrodes on the interior surfaces of the front and rear sections. The vest can be used to provide electrical muscle stimulation to muscles or nerves of the abdomen and back for users having varying body types and sizes.

Accordingly, in one embodiment, there is provided a vest for providing electrical stimulation. The vest includes a front section including a plurality of left front electrodes and a plurality of right front electrodes provided on an interior left surface and an interior right surface of the front section, respectively. A rear section is provided including a plurality of left rear electrodes and a plurality of right rear electrodes provided on an interior left surface and an interior right surface of the rear section. A controller is provided on an exterior surface of the front section for providing respective selectively adjustable electrical pulse signals to the electrodes via respective wires routed over the exterior surface of the front section and an exterior surface of the rear section to the electrodes through respective openings provided in the front and rear sections. The electrodes and the front and rear sections include means for positional adjustment of the electrodes on the interior surfaces of the front and rear sections.

Still other aspects, features, and advantages of the present invention are readily apparent from the following detailed description, simply by illustrating a number of particular embodiments and implementations, including the best mode contemplated for carrying out the present invention. The present invention is also capable of other and different embodiments, and its several details can be modified in various respects, all without departing from the spirit and scope of the present invention. Accordingly, the drawing and description are to be regarded as illustrative in nature, and not as restrictive.

BRIEF DESCRIPTION OF THE DRAWINGS

The present invention is illustrated by way of example, and not by way of limitation, in the figures of the accompanying drawing, in which like reference numerals refer to similar elements, and in which:

FIGS. 3a and 3b are diagrams of exemplary switches that can be employed in the electrode controllers of FIGS. 2a and 2b; and FIG. 4 is diagram of means for variable electrode placement that can be employed in the electrode vest of FIG. 1.

DETAILED DESCRIPTION OF THE PREFERRED EMBODIMENTS

An electrode vest for electrical stimulation of the abdomen and back is described. In the following description, for purposes of explanation, numerous specific details are set forth in order to provide a thorough understanding of the various embodiments. It is apparent to one skilled in the art, however, that the various embodiments can be practiced without these specific details or with an equivalent arrangement. In some instances, well-known structures and devices are shown in block diagram form in order to avoid unnecessarily obscuring the various embodiments.

Figure 1A:
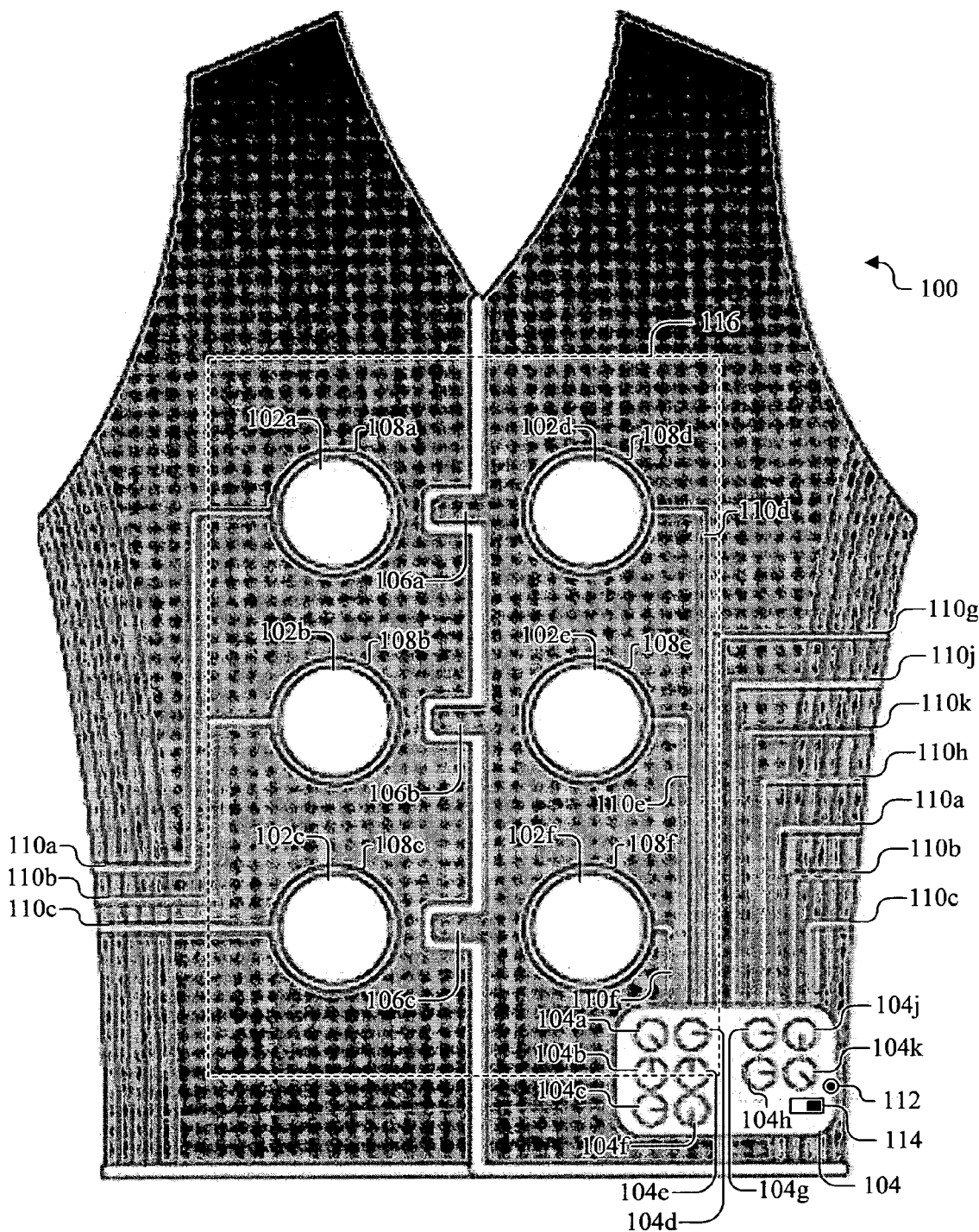
FIGS. 1a and 1b are diagrams of front and rear views of an exemplary electrode vest for electrical stimulation.
Figure 1B:
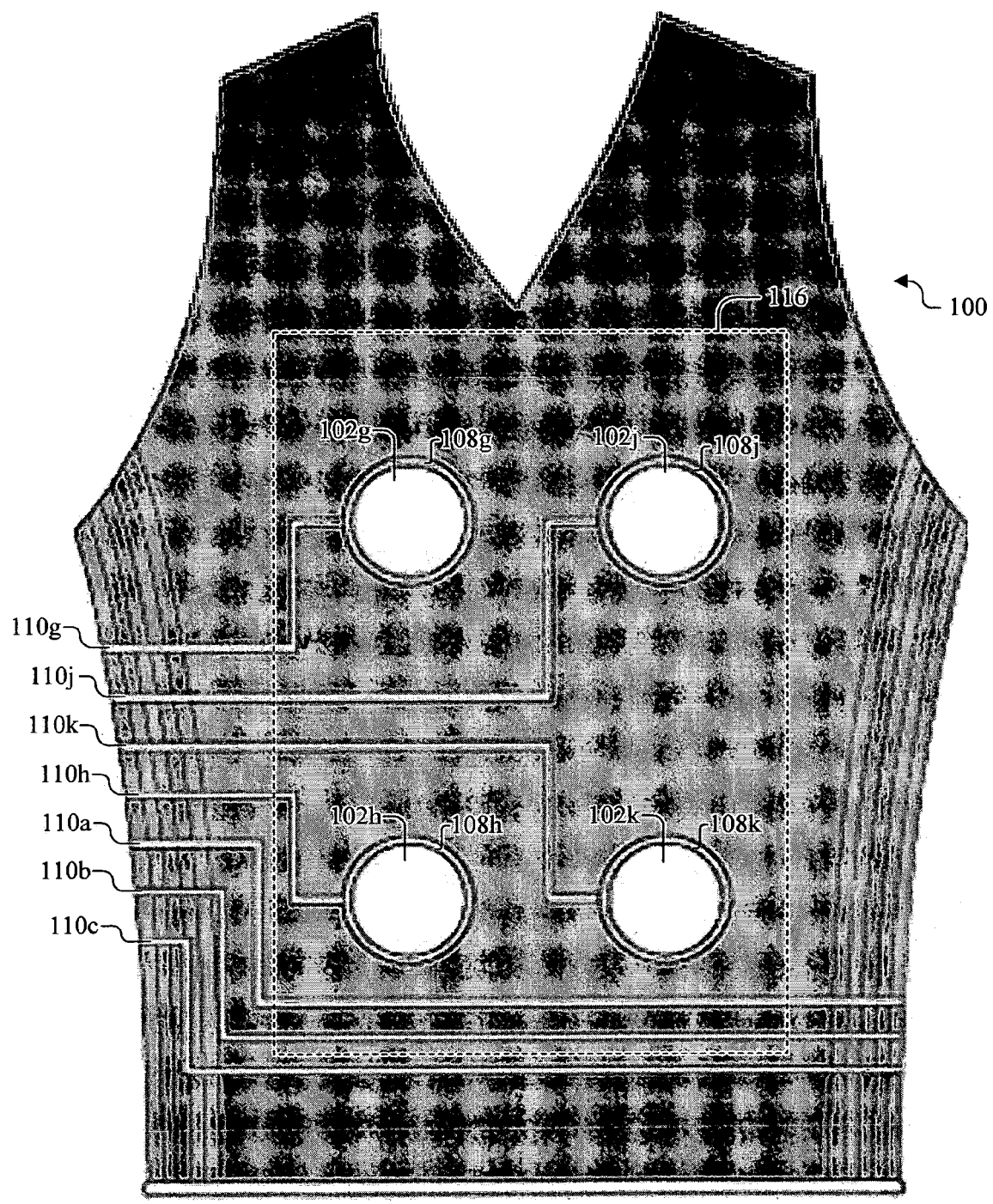

Referring now to the drawings, wherein like reference numerals designate identical or corresponding parts throughout the several views, and more particularly to FIGS. 1a and 1b thereof, there is illustrated an exemplary electrode vest 100 for electrical stimulation. As shown in FIG. 1a, the electrode vest 100 includes electrodes 102a–102c for providing electrical stimulation of the muscles or nerves on the right portion of the abdomen, and electrodes 102d–102f for providing electrical stimulation of the muscles or nerves on the left portion of the abdomen.

As shown in FIG. 1b, the electrode vest 100 includes electrodes 102g and 102h for providing electrical stimulation of the muscles or nerves on the left portion of the back, and electrodes 102j and 102k for providing electrical stimulation of the muscles or nerves on the right portion of the back. The electrodes 102a–102h, 102j, and 102k can be constructed as laminated and/or non-laminated structures, for example, including a conducting surface, and a non-conductive surface. The conductive surface can include, for example, a conductive film or sheet, a silicon-based conductive rubber sheet or film, a conductive water wicking material, a material incorporating a conductive gel, etc. The conductive surface, thus, can include any material that provides an electrical interface with the skin over the muscle or nerve being stimulated.

The electrode vest 100 includes a controller 104 (e.g., micro-controller-based, microprocessor-based, digital signal processor-based, etc.) having respective switches 104a–104h, 104j, and 104k coupled to the electrodes 102a–102h, 102j, and 102k via respective wires 110a–110h, 110j, and 110k. The controller 104, via the switches 104a–104h, 104j, and 104k, provides selective adjustment of pulse repetition frequencies and pulse amplitudes for electrical signals transmitted through the skin to the muscles over which the electrodes 102a–102h, 102j, and 102k are placed.

The controller 104 further includes a power input receptacle 112 (e.g., an RCA type jack, etc.), and an on/off switch 114 (e.g., a two position slide type switch, etc.). Power from alternating current (DC), direct current (DC), battery, rechargeable battery, etc., sources can be provided to the controller 104 via the power input receptacle 112. In one embodiment, a rechargeable battery pack is provided that can be worn by the user and provides battery power to the controller 104 via a cable from the battery pack connected to the power input receptacle 112. In another embodiment, an AC to DC converter provides DC power to the controller 104 via a cable from the AC to DC converter connected to the power input receptacle 112. In further embodiments, however, the power source (e.g., watch batteries, calculator batteries, AAA batteries, solar batteries, etc.) can be integrated directly within the controller 104, as will be appreciated by those skilled in the relevant art(s).

The electrodes 102a–102h, 102j, and 102k further include attachment portions 108a–108h, 108j, and 108k for positionally selective attachment of the electrodes 102a–102h, 102j, and 102k onto attachment areas 116 provided on an interior surface of the electrode vest 100. The attachment portions 108a–108h, 108j, and 108k and the attachment areas 116 can include hook and loop attachments, such as VELCRO™. Accordingly, in one embodiment, the attachment areas 116 include VELCRO™ loop or pile material, while the attachment portions 108a–108h, 108j, and 108k include VELCRO™ hook material, and visa versa. In other embodiments, however, other electrode attachment mechanisms providing positionally selective attachment, such as a grid of snap in place fasteners (e.g., ball and socket type fasteners), etc., can be employed, as will be appreciated by those skilled in the relevant art(s).

The electrode vest 100 further includes fasteners 106a–106c for securing the electrode vest 100 around the user. The fasteners 106a–106c can include hook and loop attachments, such as VELCRO™, snap in place fasteners, such as ball and socket type fasteners, buttons, etc.

In one embodiment, the electrode vest 100 can include, for example, six electrodes 102a–102f for providing electrical stimulation of the muscles on the left and right portion of the abdomen, and four electrodes 102g–102k for providing electrical stimulation of the muscles on the left and right portion of the back, but other electrode arrangements can be employed, as will be appreciated by those skilled in the relevant art(s).

Figure 2A:
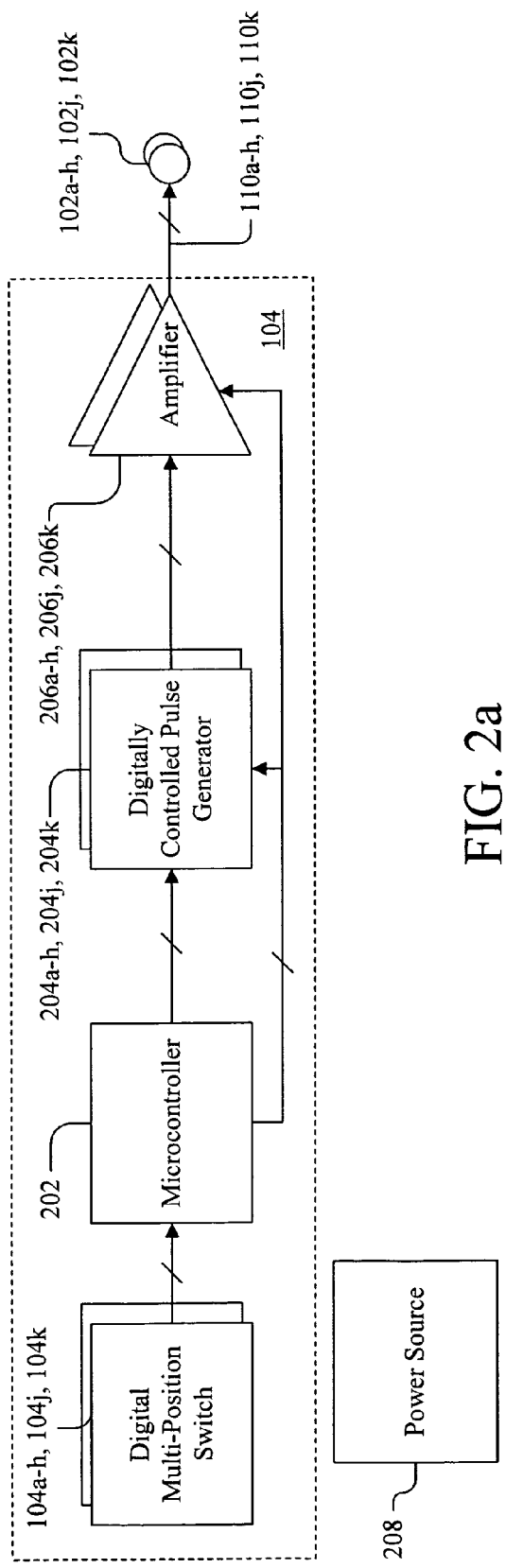
FIGS. 2a and 2b are diagrams of exemplary electrode controllers that can be employed in the electrode vest of FIG. 1.
Figure 2B:
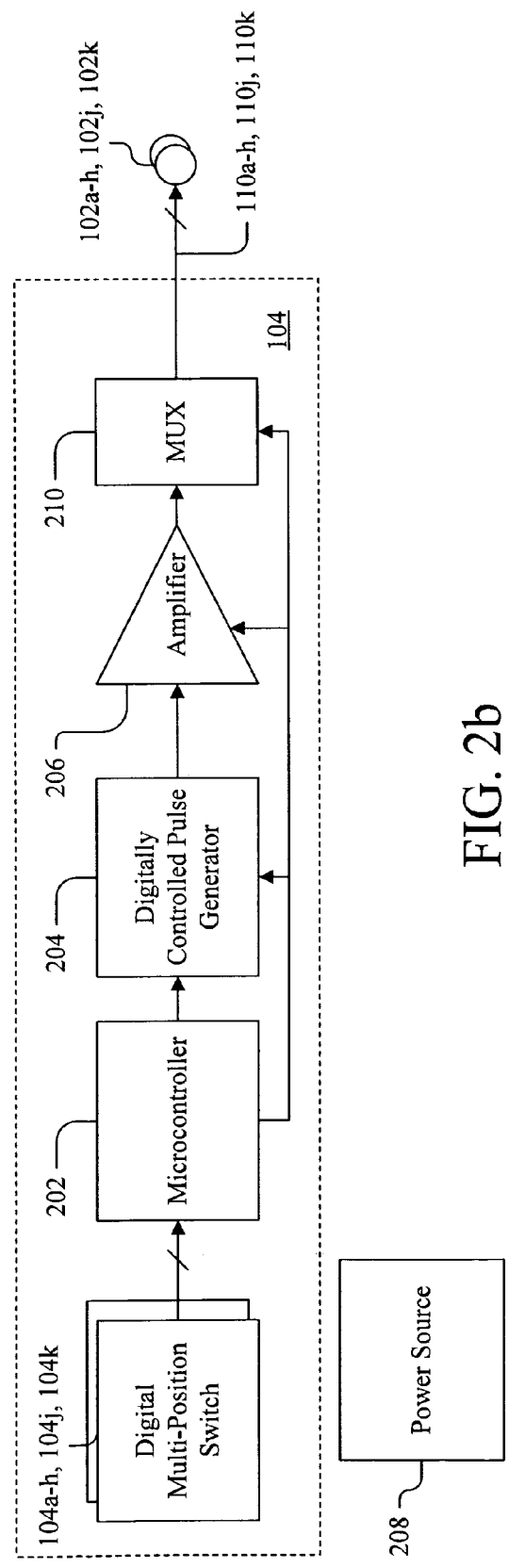

FIGS. 2a and 2b are diagrams of exemplary electrode controllers 104 that can be employed in the electrode vest 100 of FIG. 1. In FIG. 2a, the controller 104 includes the switches 104a–104h, 104j, and 104k (e.g., digital multiposition switches, etc.) coupled to a microcontroller 202. The switches 104a–104h, 104j, and 104k provide to the microcontroller 202 digital signals or commands corresponding to respective desired pulse frequency and pulse amplitude settings for the electrodes 102a–102h, 102j, and 102k set by the user. The microcontroller 202 receives respective pulse frequency selection signals from the switches 104a–104h, 104j, and 104k and appropriately controls digitally controlled pulse generators 204a–204h, 204j, and 204k to provide the desired pulse frequencies to the electrodes 102a–102h, 102j, and 102k via amplifiers 206a–206h, 206j, and 206k and wires 110a–110h, 110j, and 110k. The microcontroller 202 further receives respective pulse amplitude selection signals from the switches 104a–104h, 104j, and 104k and appropriately controls the gain of the amplifiers 206a–206h, 206j, and 206k to provide the desired pulse amplitudes to the electrodes 102a–102h, 102j, and 102k via the wires 110a–110h, 110j, and 110k.

The embodiment of FIG. 2b operates in a similar manner as the embodiment of FIG. 2a, except that the digitally controlled pulse generators 204a–204h, 204j, and 204k and the amplifiers 206a–206h, 206j, and 206k are replaced by a single digitally controlled pulse generator 204, and a single amplifier 206, by multiplexing the output from the amplifier 206 via a multiplexer 210 to provide the desired pulse frequencies and pulse amplitudes to the electrodes 102a–102h, 102j, and 102k via the wires 110a–110h, 110j, and 110k. In FIGS. 2a and 2b, a power source 208 provides power to the controller 104. The power source 208 can include a rechargeable battery pack that can be worn by the user, an AC to DC converter, other power sources, such as watch batteries, calculator batteries, AAA batteries, solar batteries, etc., and can be provided separate from or integrated directly within the controller 104, as will be appreciated by those skilled in the relevant art(s).

FIGS. 3a and 3b are diagrams of exemplary switches 104a–104h, 104j, and 104k that can be employed in the electrode controllers 104 of FIGS. 2a and 2b. In FIGS. 3a and 3b, the switches 104a–104h, 104j, and 104k are in the form of circular knobs that are mounted on a surface of an enclosure or housing 306 of the controller 104 and include dual positions 302 and 304. While the switches 104a–104h, 104j, and 104k are in a first position 302, the switches 104a–104h, 104j, and 104k can be rotated clockwise or counter clockwise by the user to increase or decrease a selected pulse frequency value transmitted to the controller 104. Similarly, while the switches 104a–104h, 104j, and 104k are in a second or depressed position 304, the switches 104a–104h, 104j, and 104k can be rotated clockwise or counter clockwise by the user to increase or decrease a selected pulse amplitude value transmitted to the controller 104.

In one embodiment, the first position 302 corresponds to the desired pulse frequency and the second position 304 corresponds to the desired pulse amplitude, with increasing values transmitted to the controller 104 based on clockwise rotation and decreasing values transmitted based on counter clockwise rotation of the switches 104a–104h, 104j, and 104k. However, in other embodiments, other types of switches and switch configurations can be employed, such as separate switches for pulse frequency and amplitude, clockwise rotation for deceasing and counter clockwise rotation for increasing values, slide type switches, etc., as will be appreciated by those skilled in the relevant art(s).

FIG. 4 is diagram detailing variable electrode 102a–102h, 102j, and 102k placement in the electrode vest 100 of FIG. 1. In FIG. 4, the electrodes 102a–102h, 102j, and 102k are selectively attachable on the electrode vest 100 on the attachment areas 116, via a hook and loop arrangement, such as VELCRO™, including the interior portions (e.g., VELCRO™ loop material) and the electrode portions 108a–108h, 108j, and 108k (e.g., VELCRO™ hook material). The wires 10a–110h, 110j, and 110k are sufficiently long and are routed from the controller 104 to the respective electrodes 102a–102h, 102j, and 102k via openings 404 provided in the electrode vest 100 and so that the skin contacting surface 402 of the electrodes 102a–102h, 102j, and 102k can be adjusted within the interior portions 116 of the electrode vest to accommodate users having varying body types and sizes.

By providing the electrodes 102a–102h, 102j, and 102k with positionally selective attachment onto the electrode vest 100, the electrode vest 100, advantageously, can be manufactured in small, medium, and large sizes, for accommodating varying body types, as compared to the background art devices. In addition, the positionally selective attachment of the electrodes 102a–102h, 102j, and 102k coupled with the six electrodes 102a–102f for electrical stimulation of the muscles of the abdomen and the four electrodes 102g–102k for electrical stimulation of the muscles of the back, provides adjustable placement of the electrodes 102a–102h, 102j, and 102k for optimal stomach and back muscle stimulation for varying body types and sizes of users of the electrode vest 100, as compared to the background art devices. Further, by providing the electrodes 102a–102h, 102j, and 102k in a vest configuration, advantageously, the electrodes 102a–102h, 102j, and 102k can be firmly secured to the muscles of the abdomen and the back of the user, even while the user is moving. Moreover, by providing a power source 208, configured as a rechargeable battery pack worn by the user (e.g., providing 60-minutes of battery power before recharging), the electrode vest 100, advantageously, can be used in remote locations, while watching TV, while reading mail and checking email, while talking on the phone, etc., all without the user being tethered to an external power supply.

The present invention (e.g., as described with respect to FIGS. 2a and 2b) can be implemented by the preparation of application-specific integrated circuits or by interconnecting an appropriate network of conventional component circuits (e.g., including one or more, microprocessors, digital signal processors, micro-controllers, etc.), as will be appreciated by those skilled in the electrical art(s). A portion of the present invention (e.g., as described with respect to FIGS. 2a and 2b) can be conveniently implemented and programmed according to the teachings of the present invention, as will be appreciated by those skilled in the computer and software art(s). Appropriate software can be readily prepared by programmers of ordinary skill based on the teachings of the present disclosure, as will be appreciated by those skilled in the software art(s).

Although the above embodiments are described in terms of incorporation into a vest, the above embodiments can be incorporated into other garments and devices, such as pants, shorts, elastic bandages and braces, etc., as will be appreciated by those skilled in the relevant art(s).

Although the above embodiments are described in terms of electrical stimulation of the muscles of the abdomen (e.g., via six electrodes) and back (e.g., via four electrodes), the above embodiments can be configured for electrical stimulation of other parts of the body, such as the chest (e.g., via an additional left front and right front electrode), shoulders (e.g., via an additional left rear and right rear electrode), etc., as will be appreciated by those skilled in the relevant art(s).

Although the above embodiments are described in terms the electrode conductive surface including a conductive film or sheet, a silicon-based conductive rubber sheet or film, a conductive water wicking material, a material incorporating a conductive gel, etc., the above embodiments can be configured to include an additional liquid or gel applied between the skin and the conductive surface, as will be appreciated by those skilled in the relevant art(s).

While the present invention has been described in connection with a number of embodiments and implementations, the present invention is not so limited, but rather covers various modifications and equivalent arrangements, which fall within the purview of the appended claims.

What is claimed is:

1. A vest for providing electrical stimulation, comprising:

a front section including a plurality of left front electrodes and a plurality of right front electrodes provided on an interior left surface and an interior right surface of the front section, respectively;

a rear section including a plurality of left rear electrodes and a plurality of right rear electrodes provided on an interior left surface and an interior right surface of the rear section; and a controller provided on an exterior surface of the front section for providing respective selectively adjustable electrical pulse signals to the electrodes via respective wires routed over the exterior surface of the front section and an exterior surface of the rear section to the electrodes through respective openings provided in the front and rear sections, wherein the electrodes and the front and rear sections include means for positional adjustment of the electrodes on the interior surfaces of the front and rear sections, and the controller includes a plurality switches for providing selectively adjustable electrical pulse frequency and amplitude signals to the electrodes wherein the switches include digital dual position rotary switches with positions corresponding to the pulse frequency and the pulse amplitude, respectively, and with clockwise and counter clockwise rotations corresponding to electrical values for the pulse frequency and the pulse amplitude signals.

2. The vest of claim 1, wherein the means for positional adjustment include hook and loop fasteners respectively provided on the electrodes and on the interior surfaces of the front and rear sections.

3. The vest of claim 1, wherein the means for positional adjustment includes an array of ball and socket fasteners respectively provided on the electrodes and on the interior surfaces of the front and rear sections.

4. The vest of claim 1, further comprising:
a power source for providing electrical power to the controller.

5. The vest of claim 4, wherein the power source includes a rechargeable battery.

6. The vest of claim 5, wherein the rechargeable battery includes a rechargeable battery pack that is worn by a user of the vest.

7. The vest of claim 1, wherein the electrodes are adapted to correspond to muscles or nerves of the abdomen or back of a user of the vest.

* * * * *